(12) United States Patent
Ishinari et al.

(10) Patent No.: US 11,693,129 B2
(45) Date of Patent: Jul. 4, 2023

(54) RADIATION IMAGING APPARATUS, RADIATION IMAGING SYSTEM, CONTROL METHOD OF RADIATION IMAGING APPARATUS, AND NON-TRANSITORY COMPUTER-READABLE STORAGE MEDIUM

(71) Applicant: CANON KABUSHIKI KAISHA, Tokyo (JP)

(72) Inventors: Yutaka Ishinari, Yokohama (JP); Tomoyuki Yagi, Chofu (JP); Yoshiaki Ishii, Kawasaki (JP); Yuki Iwabuchi, Kawasaki (JP); Kai Suzuki, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 463 days.

(21) Appl. No.: 16/919,223

(22) Filed: Jul. 2, 2020

(65) Prior Publication Data
US 2021/0011176 A1  Jan. 14, 2021

(30) Foreign Application Priority Data

Jul. 12, 2019  (JP) .................. 2019-130436

(51) Int. Cl.
*G01T 1/17* (2006.01)
*H04N 5/378* (2011.01)
*H04N 5/357* (2011.01)
*G01N 23/04* (2018.01)
*A61B 6/00* (2006.01)
(Continued)

(52) U.S. Cl.
CPC .................. *G01T 1/17* (2013.01); *A61B 6/40* (2013.01); *A61B 6/4233* (2013.01); *G01N 23/04* (2013.01); *H04N 25/617* (2023.01); *H04N 25/75* (2023.01)

(58) Field of Classification Search
CPC ........ H04N 5/369; H04N 5/378; H04N 5/357; H04N 5/3577; A61B 6/42; A61B 6/4208; A61B 6/4233; A61B 6/40; G01N 23/02; G01T 1/16; G01T 1/17
See application file for complete search history.

(56) References Cited

U.S. PATENT DOCUMENTS

| 7,227,926 B2 | 6/2007 | Kameshima et al. |
| 7,342,221 B2 | 3/2008 | Takenaka et al. |
| 7,343,000 B2 | 3/2008 | Kameshima et al. |

(Continued)

FOREIGN PATENT DOCUMENTS

JP  2016-224004  12/2016

OTHER PUBLICATIONS

U.S. Appl. No. 16/103,150, Atsushi Iwashita, filed Aug. 14, 2018.

*Primary Examiner* — John R Lee
(74) *Attorney, Agent, or Firm* — Venable LLP

(57) ABSTRACT

A radiation imaging apparatus is provided. The radiation imaging apparatus comprises a plurality of pixels used to acquire a radiation image, and a readout circuit configured to read out a signal from each of the plurality of pixels. Correction image data used for performing offset correction is acquired from the plurality of pixels in an acquisition mode associated with an estimated value of the signal and system noise generated when the readout circuit reads out the signal, the estimated value and the system noise being set according to an imaging mode by a user.

16 Claims, 4 Drawing Sheets

(51) Int. Cl.
*H04N 25/75* (2023.01)
*H04N 25/617* (2023.01)

(56) References Cited

U.S. PATENT DOCUMENTS

| | | | |
|---|---|---|---|
| 7,381,963 B2 | 6/2008 | Endo et al. |
| 7,386,089 B2 | 6/2008 | Endo et al. |
| 7,403,594 B2 | 7/2008 | Endo et al. |
| 7,408,167 B1 | 8/2008 | Kameshima et al. |
| 7,421,063 B2 | 9/2008 | Takenaka et al. |
| 7,442,939 B2 | 10/2008 | Yagi et al. |
| 7,466,345 B2 | 12/2008 | Kameshima et al. |
| 7,470,911 B2 | 12/2008 | Yagi et al. |
| 7,476,027 B2 | 1/2009 | Takenaka et al. |
| 7,491,960 B2 | 2/2009 | Takenaka et al. |
| 7,514,663 B2 | 4/2009 | Yagi et al. |
| 7,514,690 B2 | 4/2009 | Endo et al. |
| 7,532,706 B2 | 5/2009 | Kameshima et al. |
| 7,541,591 B2 | 6/2009 | Endo et al. |
| 7,550,733 B2 | 6/2009 | Endo et al. |
| 7,564,038 B2 | 7/2009 | Endo et al. |
| 7,573,038 B2 | 8/2009 | Yokoyama et al. |
| 7,573,041 B2 | 8/2009 | Kameshima et al. |
| 7,613,277 B2 | 11/2009 | Takenaka et al. |
| 7,629,587 B2 | 12/2009 | Yagi et al. |
| 7,645,995 B2 | 1/2010 | Yagi et al. |
| 7,683,337 B2 | 3/2010 | Takenaka et al. |
| 7,696,484 B2 | 4/2010 | Yokoyama et al. |
| 7,718,973 B2 | 5/2010 | Endo et al. |
| 7,724,874 B2 | 5/2010 | Kameshima et al. |
| 7,732,776 B2 | 6/2010 | Takenaka et al. |
| 7,732,778 B2 | 6/2010 | Yokoyama et al. |
| 7,750,309 B2 | 7/2010 | Endo et al. |
| 7,786,448 B2 | 8/2010 | Endo et al. |
| 7,791,034 B2 | 9/2010 | Kameshima et al. |
| 7,791,035 B2 | 9/2010 | Yokoyama et al. |
| 7,810,997 B2 * | 10/2010 | Okamura ............. A61B 6/5235 378/207 |
| 7,839,977 B2 | 11/2010 | Kameshima et al. |
| 7,847,263 B2 | 12/2010 | Yagi et al. |
| 7,850,367 B2 | 12/2010 | Takenaka et al. |
| 7,872,218 B2 | 1/2011 | Endo et al. |
| 7,880,145 B2 | 2/2011 | Yagi et al. |
| 7,965,817 B2 | 6/2011 | Kameshima et al. |
| 7,989,772 B2 | 8/2011 | Yagi et al. |
| 7,994,481 B2 | 8/2011 | Yagi et al. |
| 8,072,514 B2 | 12/2011 | Takenaka et al. |
| 8,076,647 B2 * | 12/2011 | Danielsson ............. G01T 1/00 250/370.11 |
| 8,093,562 B2 | 1/2012 | Yokoyama et al. |
| 8,107,588 B2 | 1/2012 | Kameshima et al. |
| 8,167,486 B2 | 5/2012 | Takenaka et al. |
| 8,222,611 B2 | 7/2012 | Yagi et al. |
| 8,247,779 B2 | 8/2012 | Kameshima et al. |
| 8,576,294 B2 | 11/2013 | Kameshima et al. |
| 8,723,996 B2 | 5/2014 | Yokoyama et al. |
| 8,792,024 B2 | 7/2014 | Takenaka et al. |
| 8,809,795 B2 | 8/2014 | Takenaka et al. |
| 8,829,438 B2 | 9/2014 | Sato et al. |
| 9,048,154 B2 | 6/2015 | Takenaka et al. |
| 9,128,196 B2 | 9/2015 | Sato et al. |
| 9,134,432 B2 | 9/2015 | Iwashita et al. |
| 9,234,966 B2 | 1/2016 | Sugawara et al. |
| 9,423,512 B2 | 8/2016 | Sato et al. |
| 9,445,030 B2 | 9/2016 | Yagi et al. |
| 9,462,989 B2 | 10/2016 | Takenaka et al. |
| 9,468,414 B2 | 10/2016 | Ryu et al. |
| 9,470,800 B2 | 10/2016 | Iwashita et al. |
| 9,470,802 B2 | 10/2016 | Okada et al. |
| 9,541,653 B2 | 1/2017 | Iwashita et al. |
| 9,655,586 B2 | 5/2017 | Yagi et al. |
| 9,737,271 B2 | 8/2017 | Iwashita et al. |
| 9,812,474 B2 | 11/2017 | Yagi et al. |
| 9,971,046 B2 | 5/2018 | Ryu et al. |
| 9,980,685 B2 | 5/2018 | Iwashita et al. |
| 9,989,656 B2 | 6/2018 | Sato et al. |
| 10,009,990 B2 | 6/2018 | Takenaka et al. |
| 10,055,819 B2 | 8/2018 | Asai |
| 10,197,684 B2 | 2/2019 | Terui et al. |
| 10,274,612 B2 | 4/2019 | Ishii et al. |
| 10,349,914 B2 | 7/2019 | Takenaka et al. |
| 10,416,323 B2 | 9/2019 | Ryu et al. |
| 10,551,721 B2 | 2/2020 | Sato et al. |
| 10,779,777 B2 | 9/2020 | Terui et al. |
| 10,782,251 B2 | 9/2020 | Sato et al. |
| 11,153,511 B2 * | 10/2021 | Tezuka ..................... G01T 1/17 |
| 11,490,870 B2 * | 11/2022 | Oda .................... A61B 6/5229 |
| RE49,401 E * | 1/2023 | Iwashita .................. G01T 1/16 |
| 2010/0148080 A1 | 6/2010 | Endo et al. |
| 2011/0317054 A1 | 12/2011 | Kameshima et al. |
| 2014/0239186 A1 | 8/2014 | Sato et al. |
| 2014/0361189 A1 | 12/2014 | Kameshima et al. |
| 2016/0270755 A1 | 9/2016 | Takenaka et al. |
| 2018/0063933 A1 | 3/2018 | Okada et al. |
| 2018/0128755 A1 | 5/2018 | Iwashita et al. |
| 2019/0029618 A1 | 1/2019 | Sato et al. |
| 2020/0106970 A1 | 4/2020 | Tamura et al. |
| 2020/0124747 A1 | 4/2020 | Yagi et al. |
| 2021/0011176 A1 * | 1/2021 | Ishinari ................... G01T 1/247 |
| 2021/0275127 A1 * | 9/2021 | Oda ..................... A61B 6/4233 |

* cited by examiner

FIG. 2A

| IMAGING CONDITION No. | BINNING | FRAME RATE [fps] | GAIN | IMAGE SIZE [inch] | TARGET DOSE |
|---|---|---|---|---|---|
| 1 | 1×1 | 5 | 6 | 17 | 0.5 |
| 2 | 1×1 | 7.5 | 1 | 12 | 0.75 |
| 3 | 1×1 | 7.5 | 1 | 17 | 1 |
| 4 | 2×2 | 15 | 4 | 12 | 0.25 |
| 5 | 3×3 | 30 | 3 | 9 | 0.125 |
| ... | ... | ... | ... | ... | ... |

FIG. 2B

| IMAGING MODE | IMAGING CONDITION No. | OBJECT INFORMATION | IRRADIATION CONDITION | ACQUISITION MODE |
|---|---|---|---|---|
| A | 5 | D | G | 1 |
| B | 2 | E | H | 1 |
| C | 3 | F | I | 0 |
| ... | ... | ... | ... | ... |

FIG. 3

| IMAGING MODE | IMAGING CONDITION No. | OBJECT INFORMATION | IRRADIATION CONDITION | ACQUISITION MODE |
|---|---|---|---|---|
| A' | 5 | D' | G' | 11 |
| B' | 2 | E' | H' | 11 |
| C' | 3 | F' | I' | 00 |
| ... | ... | ... | ... | ... |

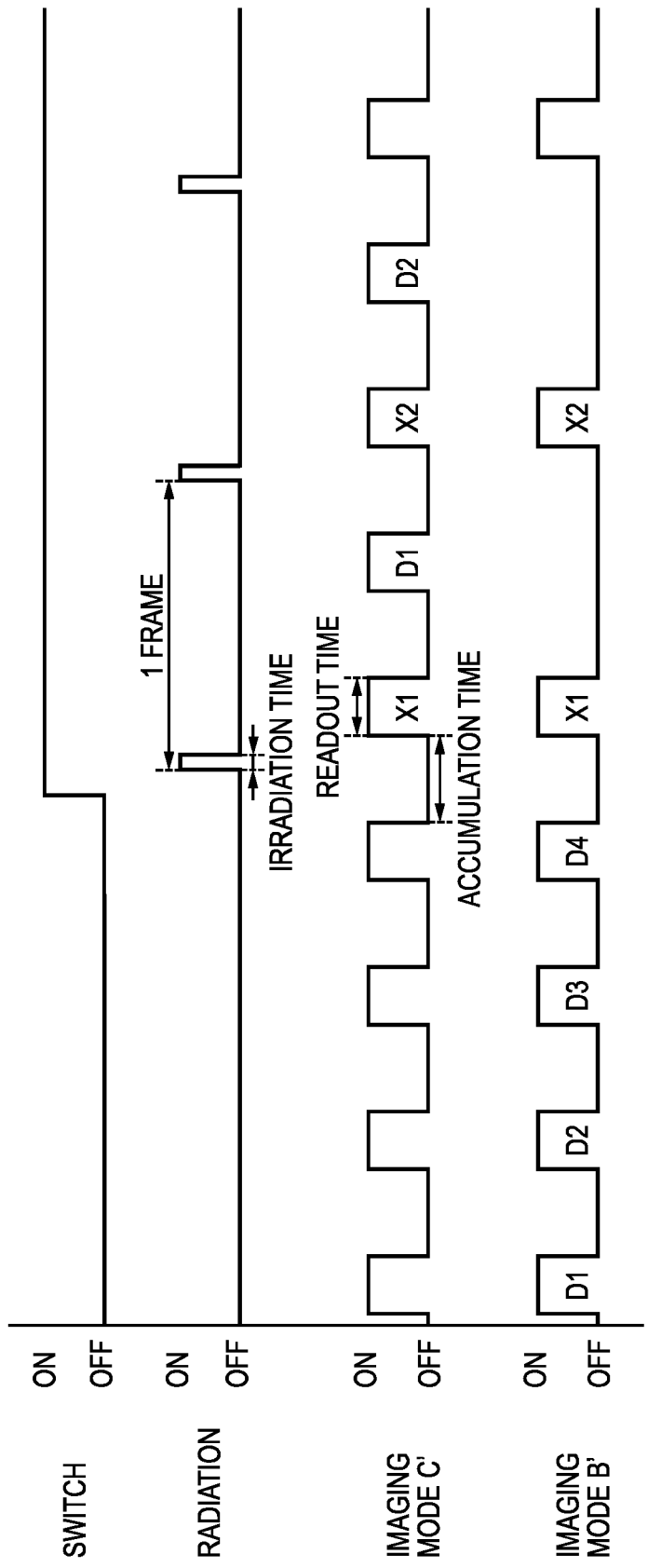

RADIATION IMAGING APPARATUS, RADIATION IMAGING SYSTEM, CONTROL METHOD OF RADIATION IMAGING APPARATUS, AND NON-TRANSITORY COMPUTER-READABLE STORAGE MEDIUM

BACKGROUND OF THE INVENTION

Field of the Invention

The present invention relates to a radiation imaging apparatus, a radiation imaging system, a control method of the radiation imaging apparatus, and a non-transitory computer-readable storage medium.

Description of the Related Art

In medical image diagnosis and nondestructive inspection, a radiation imaging apparatus using an FPD (Flat Panel Detector) made of a semiconductor material is widely used. In the FPD, if an offset component caused by electric charges remaining in a pixel, a dark current, or the like is superimposed on a signal, the image quality of the obtained radiation image can be deteriorated. Therefore, offset correction is performed to remove the offset component from the signal. Japanese Patent Laid-Open No. 2016-224004 describes that in order to reduce the afterimage of an acquired radiation image, a method of acquiring correction data for offset correction is switched in accordance with the imaging mode.

SUMMARY OF THE INVENTION

Since correction data is acquired from image data obtained by performing imaging without irradiation of radiation, it is affected by system noise generated when reading out a signal, such as noise caused by a transistor reading out the image data or the like. Japanese Patent Laid-Open No. 2016-224004 describes that in order to reduce an afterimage, imaging of an object and acquisition of correction data are alternately repeated. When image data acquired in one imaging operation to acquire correction data is used as the correction data, the influence of system noise on the correction data can be larger than in a case in which the correction data is acquired by, for example, adding and averaging a plurality of image data. If the influence of system noise on the correction data is large, the accuracy of offset correction can be decreased, and the quality of the obtained radiation image can be deteriorated.

Each of some embodiments of the present invention provides a technique advantageous in suppressing a deterioration in image quality of a radiation image.

According to some embodiments, a radiation imaging apparatus comprising: a plurality of pixels used to acquire a radiation image; and a readout circuit configured to read out a signal from each of the plurality of pixels, wherein correction image data used for performing offset correction is acquired from the plurality of pixels in an acquisition mode associated with an estimated value of the signal and system noise generated when the readout circuit reads out the signal, the estimated value and the system noise being set according to an imaging mode by a user, is provided.

According to some other embodiments, a radiation imaging apparatus comprising: a plurality of pixels used to acquire a radiation image; and a determination unit configured to determine an acquisition mode for acquiring correction image data from the plurality of pixels to perform offset correction, wherein the acquisition mode includes a first mode in which the correction image data is acquired based on a plurality of image data obtained without irradiation of radiation, and a second mode in which the correction image data is acquired based on one image data obtained without radiation of irradiation, and the determination unit acquires an estimated incident dose based on an imaging mode set by a user, the determination unit determines the acquisition mode to be the first mode if the incident dose is not larger than a preset first threshold value, and determines the acquisition mode to be the second mode if the incident dose is larger than the preset first threshold value, is provided.

According to still other embodiments, a control method of a radiation imaging apparatus including a plurality of pixels used to acquire a radiation image, and a readout circuit configured to read out a signal from each of the plurality of pixels, comprising: acquiring, to perform offset correction, correction image data from the plurality of pixels in an acquisition mode associated with an estimated value of the signal based on an imaging mode set by a user and system noise generated when the readout circuit reads out the signal, is provided.

According to yet other embodiments, a non-transitory computer-readable storage medium storing a program for causing a computer to execute a control method of a radiation imaging apparatus including a plurality of pixels used to acquire a radiation image, and a readout circuit configured to read out a signal from each of the plurality of pixels, comprising: acquiring, to perform offset correction, correction image data from the plurality of pixels in an acquisition mode associated with an estimated value of the signal based on an imaging mode set by a user and system noise generated when the readout circuit reads out the signal, is provided.

Further features of the present invention will become apparent from the following description of exemplary embodiments (with reference to the attached drawings).

BRIEF DESCRIPTION OF THE DRAWINGS

FIGS. 2A and 2B are tables for explaining imaging modes of the radiation imaging apparatus shown in FIG. 1B;

FIG. 3 is a table showing an example of combinations each including the imaging mode of the radiation imaging apparatus shown in FIG. 1B and a method of offset correction;

FIG. 5 is a timing chart showing the example of the operation of the radiation imaging apparatus shown in FIG. 1B.

DESCRIPTION OF THE EMBODIMENTS

Figure 1A:
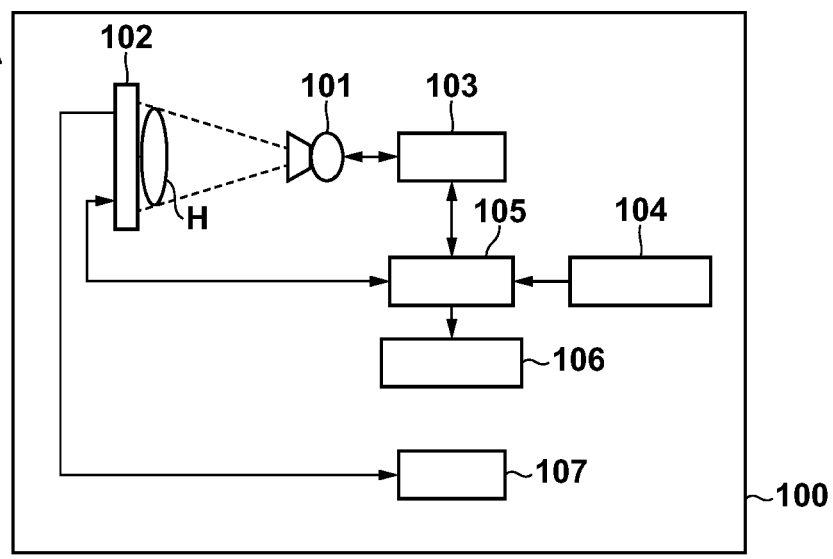
FIGS. 1A and 1B are views showing an arrangement example of a radiation imaging system using a radiation imaging apparatus according to the first embodiment.

Hereinafter, embodiments will be described in detail with reference to the attached drawings. Note, the following embodiments are not intended to limit the scope of the claimed invention. Multiple features are described in the embodiments, but limitation is not made an invention that requires all such features, and multiple such features may be combined as appropriate. Furthermore, in the attached drawings, the same reference numerals are given to the same or similar configurations, and redundant description thereof is omitted.

Radiation in the present invention can include α-rays, β-rays, γ-rays, and the like which are beams generated by particles (including photons) emitted by radiation decay, as well as beams having the similar or higher energy, for example, X-rays, particle beams, cosmic rays, and the like.

With reference to FIGS. 1A to 2B, the arrangement and operation of a radiation imaging apparatus 102 according to the first embodiment will be described. FIG. 1A is a schematic view showing an arrangement example of a radiation imaging system 100 using the radiation imaging apparatus 102 according to this embodiment. In this embodiment, the radiation imaging apparatus 102 is mainly used for medical purposes, and captures radiation images based on various types of imaging procedures for radiation imaging.

In the arrangement shown in FIG. 1A, the radiation imaging system 100 includes a radiation source 101, the radiation imaging apparatus 102, a tube bulb control unit 103, an imaging mode setting unit 104, a system control unit 105, a mode display unit 106, and an image display unit 107. The radiation source 101 irradiates the radiation imaging apparatus 102 with radiation via an object H. The radiation imaging apparatus 102 includes a plurality of pixels used to detect the radiation having passed through the object H and entering the radiation imaging apparatus 102 to acquire a radiation image, and generates radiation image data.

The tube bulb control unit 103 controls the irradiation condition of radiation emitted from the radiation source 101 in accordance with the system control unit 105. The irradiation condition of radiation includes the tube voltage, the tube current, the irradiation time, the radiation output format, and the like of the radiation source 101. The radiation output format includes, for example, a pulse output used when capturing a still image or the like, and a continuous output used when capturing a moving image or the like.

The imaging mode setting unit 104 can be an input device for a user (a doctor, a technician, or the like) to input an imaging mode in accordance with the imaging procedure or the like. The imaging mode includes an imaging condition and object information in addition to the irradiation condition described above. The imaging condition includes the frame rate upon capturing a radiation image, the number of binning upon capturing a radiation image, the image size of a radiation image, the gain upon amplifying a signal output from each of the plurality of pixels that detect radiation, and the target dose in a region of interest. The image size of a radiation image may correspond to a region to be irradiated with radiation in the radiation imaging apparatus 102. The imaging condition can further include a time required to read out signals from the plurality of pixels, a time required for the pixels to accumulate electric charges generated by irradiation of radiation, and the like. Thus, the imaging condition is the condition related to the settings of the radiation imaging apparatus 102 when acquiring a radiation image. The object information is information related to the object H, such as the part of the object H to be imaged and the thickness of the object. The user may individually set these conditions and information of the imaging mode using the imaging mode setting unit 104, or may set the imaging mode by selecting a recipe registered in a memory of the imaging mode setting unit 104 or the like.

The system control unit 105 controls the radiation imaging apparatus 102 and the tube bulb control unit 103 in accordance with the imaging mode set by the imaging mode setting unit 104. That is, it can be said that the system control unit 105 controls the entire radiation imaging system 100. The mode display unit 106 displays the information of the imaging mode input to the imaging mode setting unit 104 by the user. The image display unit 107 displays a radiation image based on radiation image data generated by the radiation imaging apparatus 102. A doctor can use the displayed radiation image for diagnosis or the like.

Figure 1B:
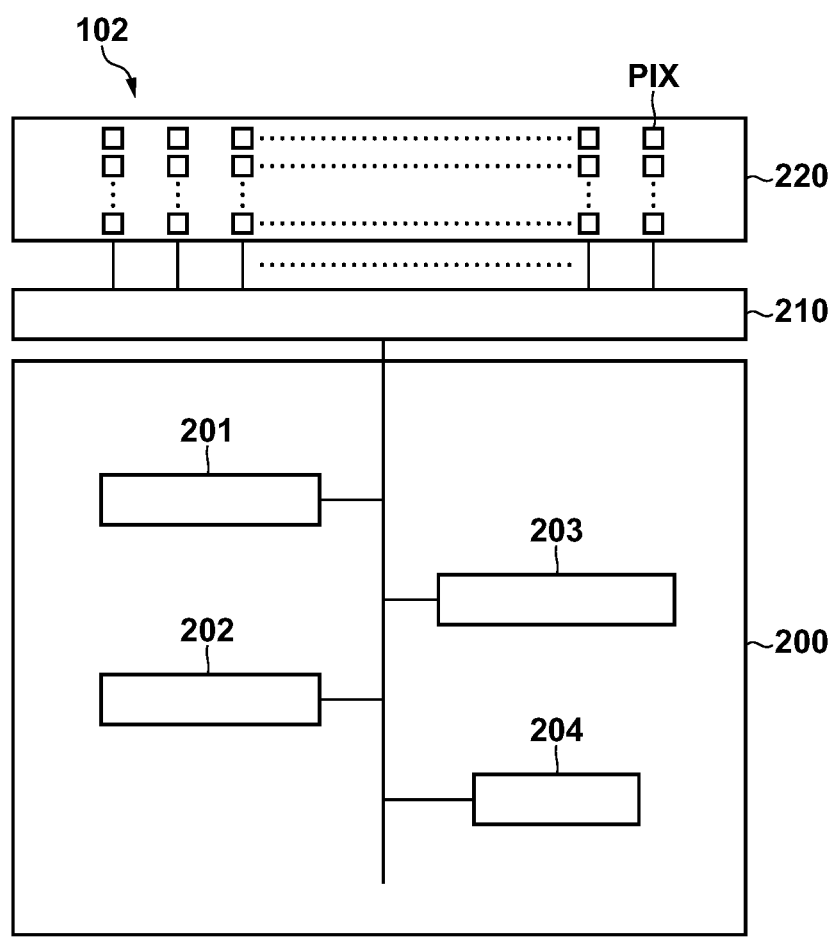

Next, the radiation imaging apparatus 102 according to this embodiment will be described with reference to FIG. 1B. The radiation imaging apparatus 102 includes a pixel array 220 including a plurality of pixels PIX used to acquire a radiation image. The radiation imaging apparatus 102 also includes a readout circuit 210 for reading out a signal by driving the pixel PIX arranged in the pixel array 220 and outputting radiation image data. The readout circuit 210 can include an amplifier circuit that amplifies the signal output from the pixel PIX, an A/D converter that digitizes the amplified signal, and the like. Further, the radiation imaging apparatus 102 according to this embodiment includes a correction unit 200 for performing offset correction on the signal output from the pixel PIX.

The pixel PIX can include a conversion element that converts incident radiation into electric charges, and a switch element that outputs an electric signal according to the electric charges generated by the conversion element. For example, the conversion element can be formed by a scintillator that converts incident radiation into light and a photoelectric conversion element that converts the converted light into electric charges. The photoelectric conversion element may be a PIN photodiode or a MIS photodiode, which is arranged on an insulating substrate such as a glass substrate and whose main material is amorphous silicon. The conversion element is not limited to the indirect conversion element as described above, and may be a direct conversion element that directly converts radiation into electric charges.

When imaging a radiation image, the pixel array 220 outputs image data, which is a signal corresponding to the amount of incident radiation, in accordance with an operation of the readout circuit 210. The image data read out by the readout circuit 210 undergoes offset correction in the correction unit 200, and is output from the radiation imaging apparatus 102 as radiation image data.

Next, the correction unit 200 will be described. The correction unit 200 includes an image data acquisition unit 201, a correction image data acquisition unit 202, a determination unit 203, and a processing unit 204. The image data acquisition unit 201 holds image data output from each of the plurality of pixels PIX arranged in the pixel array 220 in accordance with the incident radiation during irradiation of radiation. The image data output from each pixel PIX of the pixel array 220 includes an offset component. The offset component can include a component caused by residual charges or dark current charges, fixed noise, or the like. The correction image data acquisition unit 202 holds correction image data output from each of the plurality of pixels PIX arranged in the pixel array 220 without being irradiated with radiation. The determination unit 203 determines an acquisition mode for acquiring correction image data from the plurality of pixels PIX arranged in the pixel array 220 to perform offset correction. The processing unit 204 removes the offset component from the image data held in the image data acquisition unit 201 using the correction image data held in the correction image data acquisition unit 202. The radiation image data with the offset component removed by the processing unit 204 is, for example, transmitted to the image display unit 107 and displayed as a radiation image.

Next, the conditions and information set by the imaging mode setting unit 104 will be described with reference to FIGS. 2A and 2B. FIG. 2A is a table showing an example of parameters of an imaging condition included in the imaging mode. As described above, the imaging condition includes the frame rate, the number of binning, the gain upon amplifying the signal output from the pixel PIX, the image size, the target dose, and the like. Here, a description will be provided while assuming that the user selects an imaging mode such as an imaging condition from the recipe stored in the memory of the imaging mode setting unit 104. In FIG. 2A, the gain and the target dose are shown using relative values with the parameter of imaging condition No. 3 set to 1. The radiation imaging apparatus 102 can perform imaging under a plurality of imaging conditions, and the imaging condition suitable for the imaging procedure is selected and used. FIG. 2B is a table showing an example of combinations each including the imaging condition, the object information, and the irradiation condition according to the imaging mode. The acquisition mode for acquiring offset image data used in offset correction is determined in accordance with the combination of these conditions and information.

Here, the acquisition mode of the offset image data will be described. The offset image data is acquired using a method of alternately performing acquisition of image data for a radiation image and acquisition of offset image data (to be sometimes referred to as an intermittent method hereinafter) or a method of acquiring offset image data before or after capturing a radiation image (to be sometimes referred to as a fixed method hereinafter).

The fixed method enables an increase in frame rate, and can be used for capturing a moving image and high-speed continuous imaging. However, among offset components, a component caused by dark current charges or the like changes in accordance with the temperature of the radiation imaging apparatus 102, the imaging condition, or the like. Therefore, with the fixed method, the accuracy of offset correction processing may not be sufficiently obtained.

On the other hand, the intermittent method can acquire correction image data following a change in temperature or the like, so that an offset component such an afterimage can be effectively reduced, but the frame rate becomes low. Further, even if the intermittent method is selected to reduce the afterimage, in a region in which the system noise generated when the readout unit reads out a signal from the pixel PIX is more dominant than the noise (to be sometimes referred to as quantum noise hereinafter) caused by irradiation of radiation, the S/N ratio (signal-noise ratio) may be deteriorated. Here, the readout unit includes the switch element included in each pixel PIX arranged in the pixel array 220, the readout circuit 210, and the like, and refers to the entire path for reading out a signal from the pixel PIX arranged in the pixel array 220. Therefore, the system noise can be noise generated in the readout unit, that is, the path from the pixel PIX of the pixel array 220 to the A/D converter of the readout circuit 210 where the signal is converted into digital data.

In the fixed method, correction image data is obtained by adding and averaging a plurality of image data acquired without irradiation of radiation before or after imaging a radiation image. On the other hand, in the intermittent method, one image data acquired without irradiation of radiation is used as correction image data. Therefore, in correction processing using correction image data obtained by adding and averaging a plurality of image data and correction processing using correction image data based on one image data, system noise becomes large in the latter case.

For example, when the dose of applied radiation is small, the signal value of the generated signal is small, so that the system noise can be dominant. That is, in the imaging mode in which a region of interest has a low dose, the S/N ratio is lower in the intermittent method than in the fixed method.

Accordingly, in this embodiment, correction image data used for performing offset correction is acquired from the plurality of pixels PIX in the acquisition mode associated with the estimated value of the signal and the system noise generated when the readout unit reads out the signal, the estimated value and the system noise according to the imaging mode set by the user. In FIG. 2B, the acquisition modes are represented by "1" and "0". "1" represents the acquisition mode in which the above-described fixed method is used to acquire correction image data based on a plurality of image data obtained without irradiation of radiation. "0" represents the acquisition mode in which the above-described intermittent method is used to acquire correction image data based on one image data obtained without irradiation of radiation.

The determination unit 203 acquires the estimated incident dose based on the imaging mode set by the user and, if the incident dose is equal to or smaller than a preset threshold value, determines the acquisition mode to be the "1" mode. If the incident dose is larger than the preset threshold value, the determination unit 203 determines the acquisition mode to be the "0" mode. According to this, the radiation imaging apparatus 102 acquires correction image data. The threshold value for determining the acquisition mode is set in accordance with the system noise generated when the above-described readout unit reads out signals from the plurality of pixels PIX arranged in the pixel array 220. The correction image data may be acquired before or after a radiation image to be corrected using the correction image data is captured.

Accordingly, in the imaging mode in which it is required to prevent a deterioration of the S/N ratio, the determination unit 203 selects the "1" mode as the acquisition mode. For example, in the imaging mode in which a region of interest has a low dose and the signal value of the signal output from the pixel PIX arranged in the pixel array 220 is small, the system noise is more dominant than the radiation-induced quantum noise. Therefore, in order to secure the S/N ratio, the "1" mode is selected as the mode for acquiring correction image data. This enables highly accurate correction in the offset correction processing performed by the processing unit 204. As a result, a radiation image with good image quality can be acquired.

The determination unit 203 acquires the estimated incident dose based on at least one of the number of binning upon capturing a radiation image, the gain upon amplifying a signal output from the pixel PIX, the target dose in a region of interest, the object information, the tube current of the radiation source 101 that irradiates the radiation imaging apparatus 102 with radiation, the tube voltage of the radiation source 101, or the radiation irradiation time, all of which are included in the imaging mode described above. For example, when the number of binning increases, signals output from many pixels PIX are used by being added and averaged, so that the influence of the system noise can be reduced. In addition, the signal value obtained from the signal output from each pixel PIX largely changes in accordance with the number of binning or the gain. For example, if the number of binning or the gain is doubled, the obtained signal value is also expected to be almost doubled. The target dose can change in accordance with the combination of the number of binning and the gain. When the target dose is small, the signal value of the signal output from the pixel PIX can be small. When the thickness of the object H increases, the amount of incident radiation decreases, so that the signal value of the signal output from the pixel PIX can be small. The amount of incident radiation can be estimated from the tube current of the radiation source 101 and the radiation irradiation time. Further, the transmittance of radiation passing through the object H changes in accordance with the tube voltage of the radiation source 101. For example, when the tube voltage is high, the transmittance of radiation passing through the object H increases, so that the amount of incident radiation can increase. Based on one or a combination of these parameters, the determination unit 203 determines the acquisition mode for acquiring correction image data.

For example, the imaging condition of an imaging mode A shown in FIG. 2B is a condition with the small target dose. Accordingly, the determination unit 203 determines the acquisition mode for acquiring correction image data to be the "1" mode. Imaging modes B and C have the same number of binning, the same frame rate, and the same gain, but different image sizes and target doses. Here, focusing on the target dose, the determination unit 203 selects the "1" mode as the acquisition mode when the target dose is 0.75, and selects the "0" mode as the acquisition mode when the target dose is 1. In this case, for example, the threshold value described above may be 0.8 at the target dose.

As has been described above, the determination unit 203 determines the acquisition mode for acquiring correction image data used for performing offset correction from the estimated value of the signal output from the pixel PIX or the estimated incident dose based on the imaging mode set by the user. Thus, even under a condition in which the signal value of the signal output from the pixel PIX is small so that it is difficult to secure the S/N ratio, the accuracy of offset correction can be increased and the image quality of the obtained radiation image can be improved.

In this embodiment, it has been described that the determination unit 203 determines the acquisition mode based on the incident dose estimated from the imaging mode set by the user, but the determination unit 203 may include, for example, a lookup table of the acquisition mode according to the imaging mode. The acquisition mode corresponding to each of the imaging recipes stored in the memory of the imaging mode setting unit 104 may be recorded in the lookup table. Further, for example, the acquisition mode based on at least one of the number of binning, the target dose, the object information, the tube current of the radiation source 101, or the radiation irradiation time, all of which are included in the imaging mode described above may be recorded. Furthermore, for example, the user may appropriately select the acquisition mode.

Further, in this embodiment, the correction unit 200 arranged in the radiation imaging apparatus 102 performs each processing of offset correction described above, but the function of the correction unit 200 is not limited to be provided in the radiation imaging apparatus 102. For example, the system control unit 105 may have the function of the correction unit 200. In this case, the radiation imaging apparatus 102 and the function of the correction unit 200 that the system control unit 105 has can be collectively referred to as the "radiation imaging apparatus" according to this embodiment. When the system control unit 105 has the function of the correction unit 200, for example, the radiation imaging apparatus 102 converts image data and correction image data output from each pixel PIX of the pixel array 220 into digital data and transmits the digital data to the system control unit 105. The system control unit 105 may correct the image data received from the radiation imaging apparatus 102 using the correction image data, transmit the generated radiation image data to the image display unit 107, and display the radiation image on the image display unit 107.

The arrangement and operation of a radiation imaging apparatus 102 according to the second embodiment will be described with reference to FIGS. 3 to 5. In the first embodiment described above, it has been described that the acquisition mode of correction image data used for performing offset correction is determined while focusing on the S/N ratio. On the other hand, in this embodiment, the acquisition mode of correction image data used for performing offset correction is determined while focusing on not only the S/N ratio but also the frame rate required for the imaging procedure and the afterimage generated in the radiation image due to irradiation of radiation. Since the arrangement of the radiation imaging apparatus 102 may be similar to that in the first embodiment described above, the description thereof is omitted here, and points different from the first embodiment will be mainly described.

FIG. 3 is a table showing an example of combinations each including the imaging condition, the object information, and the irradiation condition according to the imaging mode. In the acquisition modes shown in FIG. 3, "11" represents the acquisition mode in which the above-described fixed method is used to acquire correction image data based on a plurality of image data obtained without irradiation of radiation. "00" represents the acquisition mode in which the above-described intermittent method is used to acquire correction image data based on one image data obtained without irradiation of radiation.

Next, an operation for performing offset correction of the radiation imaging apparatus 102 according to this embodiment will be described with reference to FIG. 4. FIG. 4 is a flowchart illustrating an example of the operation of the radiation imaging apparatus 102.

First, in step S101, an imaging condition is set by a user operating an imaging mode setting unit 104. The imaging condition is transmitted to the radiation imaging apparatus 102 via a system control unit 105. Further, the imaging condition may be transmitted to a radiation source 101 via the system control unit 105 and a tube bulb control unit 103. At this time, the imaging condition may be displayed on a mode display unit 106 so that the user can select the imaging condition from a plurality of recipes and the user can check the selected imaging condition.

Then, in step S102, object information is set by the user operating the imaging mode setting unit 104. The object information is transmitted to the radiation imaging apparatus 102 via the system control unit 105. At this time, the object information may be displayed on the mode display unit 106 so that the user can check the input object information.

Then, in step S103, an irradiation condition is set by the user operating the imaging mode setting unit 104. The irradiation condition is transmitted to the radiation imaging apparatus 102 via the system control unit 105. Further, the irradiation condition is transmitted to the radiation source 101 via the system control unit 105 and the tube bulb control unit 103. At this time, the irradiation condition may be displayed on the mode display unit 106 so that the user can select the irradiation condition from a plurality of recipes and the user can check the selected irradiation condition.

It is described here that in order to set an imaging mode, the imaging condition, the object information, and the irradiation condition are set in steps S101, S102, and S103, respectively, in this order, but the present invention is not limited thereto. The order of setting the conditions and information may be any order. Further, for example, the user may select the imaging mode from recipes each including the information and conditions. Furthermore, for example, the imaging mode setting unit 104 may automatically set an appropriate irradiation condition by the user setting the imaging condition and the object information.

When the imaging mode is set, a determination unit 203 starts an operation for determining the acquisition mode for acquiring correction image data from step S104. First, in step S104, the determination unit 203 determines, based on the imaging condition, particularly the frame rate, of the imaging mode set in step S101, whether the "00" mode can be selected as the acquisition mode for acquiring correction image data used for performing offset correction. In step S104, if the frame rate is higher than a preset threshold value (NO in step S104), the determination unit 203 determines the acquisition mode to be the "11" mode (step S108). That is, if the frame rate is high and the time between imaging of a radiation image and imaging of a next radiation image is short so that acquisition of correction image data is physically impossible, offset correction is performed using the above-described fixed method.

If the determination unit 203 determines in step S104 that the "00" mode can be selected as the acquisition mode (YES in step S104), that is, if the frame rate is equal to or smaller than the preset threshold value, the determination unit 203 transitions to step S105. In step S105, the determination unit 203 determines, based on the imaging mode set in steps S101 to S103, whether an afterimage is conspicuous in an obtained radiation image. At this time, the determination unit 203 may perform determination based on a combination of the imaging condition, the object information, and the irradiation condition, or may perform determination based on any one of the conditions and information.

Here, an afterimage in a radiation image will be described. When the contrast is high in a radiation image, the boundary of an imaged part is conspicuous, so that the influence of the afterimage can be large. Therefore, in step S105, the determination unit 203 determines the acquisition mode for acquiring correction image data, based on the contrast information of the radiation image estimated from the imaging mode set by the user.

For example, if a contrast corresponding value based on the contrast information is higher than a preset threshold value (YES in step S105), the influence of the afterimage is large, so that the determination unit 203 determines the acquisition mode to be the "00" mode (step S106). Here, the contrast information includes at least one of the image size of a radiation image, the tube voltage of the radiation source 101 that irradiates the radiation imaging apparatus 102 with radiation, the object information, or the information of the gain upon amplifying signals output from a plurality of pixels PIX arranged in a pixel array 220, all of which are included in the imaging mode.

When the image size is large, the area in which the radiation directly enters the radiation imaging apparatus 102 without passing through an object H and can be large. In this case, the contrast of the radiation image can be high. Therefore, if the image size as the contrast corresponding value is larger than a predetermined threshold value, the determination unit 203 determines the acquisition mode for acquiring correction image data to be the "00" mode.

When the tube voltage of the radiation source 101 is high, the transmittance of radiation passing through the object H increases, and the contrast can decrease. On the other hand, when the tube voltage of the radiation source 101 is low, the transmittance decreases and the contrast can increase. Therefore, if the reciprocal of the tube voltage value as the contrast corresponding value is larger than a predetermined threshold value, the determination unit 203 determines the acquisition mode for acquiring correction image data to be the "00" mode.

Similarly, regarding the imaged part and the thickness of the object in the object information, contrast corresponding values corresponding to the contrast levels are set. That is, "1" may be set as the contrast corresponding value for a part where a high-contrast radiation image is obtained, and "0" may be set as the contrast corresponding value for a part where a low-contrast radiation image is obtained. In addition, when the thickness of the object is large, the contrast can decrease. For example, if the thickness of the object is equal to or smaller than 25 cm, "1" may be set as the contrast corresponding value, and if the thickness of the object is larger than 25 cm, "0" may be set as the contrast corresponding value. Thus, if the contrast corresponding value is larger than a predetermined threshold value (0 in this case), the determination unit 203 determines the acquisition mode for acquiring correction image data to be the "00" mode.

Similarly, regarding the gain, when the gradation width of the radiation image is increased by the gain, the contrast can increase. Therefore, an appropriate contrast corresponding value is set according to the gain, and if the image size as the contrast corresponding value is larger than a predetermined threshold value, the determination unit 203 determines the acquisition mode for acquiring correction image data to be the "00" mode.

In step S105, if the determination unit 203 determines that the "00" mode cannot be selected as the acquisition mode (NO in step S105), for example, if the contrast corresponding value described above is equal to or smaller than the preset threshold value, the determination unit 203 transitions to step S107.

In step S107, the determination unit 203 acquires the estimated incident dose based on the imaging mode set by the user, as in the first embodiment described above. Based on the estimated incident dose, the determination unit 203 determines the acquisition mode associated with the estimated value of the signal output from the pixel PIX arranged in the pixel array 220 and the system noise generated when the readout unit reads out the signal. The determination unit 203 acquires the estimated incident dose based on the imaging mode set by the user and, if the incident dose is equal to or smaller than a preset threshold value (NO in step S107), determines the acquisition mode to be the "11" mode (step S108). If the incident dose is larger than the preset threshold value (YES in step S107), the determination unit 203 determines the acquisition mode to be the "00" mode (step S106).

After the determination unit 203 has determined, in steps S104 to S108, the acquisition mode for acquiring correction data used for performing offset correction, irradiation of radiation is started in step S109. For example, the radiation imaging apparatus 102 transmits an exposure permission signal to the system control unit 105 in response to the determination of the acquisition mode by the determination unit 203. When the system control unit 105 having received the exposure permission signal instructs the radiation source 101 to start irradiation of radiation via the tube bulb control unit 103, irradiation of radiation from the radiation source 101 in accordance with the irradiation condition set in step S103 can be started. The radiation imaging apparatus 102 acquires image data in step S110 in accordance with the imaging mode set in steps S101 to S103.

After the image data is acquired, in step S111, correction data used for performing offset correction is acquired without irradiation of radiation in the acquisition mode determined by the determination unit 203. When imaging a moving image, steps S110 and S111 can be repeated. In the arrangement shown in FIG. 4, the correction image data is acquired after the image data is acquired, but the correction image data may be acquired before the image data is acquired.

After the image data and the correction image data are acquired, offset correction is performed by a processing unit 204 in step S112. Then, in step S113, radiation image data having undergone the offset correction is output from the radiation imaging apparatus 102 and, for example, a radiation image is displayed on an image display unit 107.

Figure 4:
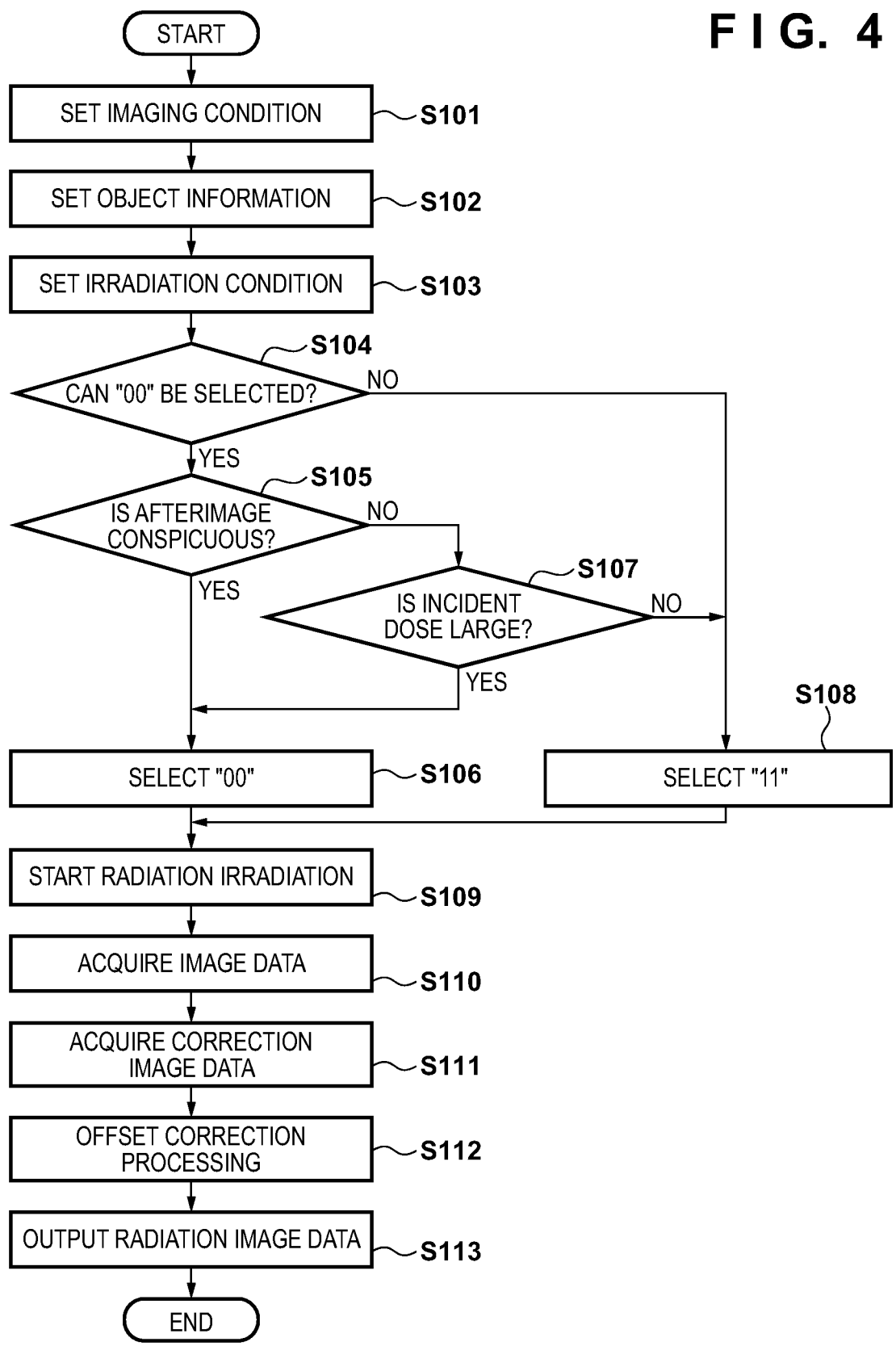
FIG. 4 is a flowchart illustrating an example of an operation of the radiation imaging apparatus shown in FIG. 1B.

In the arrangement shown in FIG. 4, determination in step S107 is performed if the contrast corresponding value based on the contrast information is equal to or smaller than the preset threshold value in step S105 (NO in step S105), but the present invention is not limited thereto. Determination in step S105 may be omitted, and determination in step S107 may be performed if the determination unit 203 determines in step S104 that the "00" mode can be selected as the acquisition mode (YES in step S104). That is, the determination unit 203 may determine, using the frame rate and the estimated incident dose, the acquisition mode for acquiring correction data used for performing offset correction.

Next, the operation timing of the radiation imaging apparatus 102 will be described with reference to FIG. 5. FIG. 5 shows a timing chart of a case in which the frame rate does not change but the method of acquiring correction image data is changed, as in imaging modes B' and C' shown in FIG. 3. Here, a case in which continuous imaging such as imaging of a moving image is performed will be described.

The first row from the top of FIG. 5 shows the state of an exposure switch used by the user to request a start of radiation irradiation. "ON" indicates that the exposure switch is pressed by the user. The second row from the top shows the timing at which radiation is emitted from the radiation source 101. "ON" indicates that radiation is emitted. The third row from the top shows the operation of the pixel PIX arranged in the pixel array 220 of the radiation imaging apparatus 102 in a case in which the imaging mode C' shown in FIG. 3 is set. The fourth row from the top shows the operation of the pixel PIX arranged in the pixel array 220 of the radiation imaging apparatus 102 in a case in which the imaging mode B' shown in FIG. 3 is set. "ON" indicates that a signal is read out from the pixel PIX. That is, "ON" indicates that the switch element of the conversion element is conductive.

When the imaging mode C' shown in FIG. 3 is set by the user using the imaging mode setting unit 104, the determination unit 203 determines the acquisition mode for acquiring correction image data to be the "00" mode in accordance with the flowchart of FIG. 4 described above. When the imaging mode B' is set, the determination unit 203 determines the acquisition mode for acquiring correction image data to be the "11" mode in accordance with the flowchart of FIG. 4.

When the imaging mode C' is set and the user presses the exposure switch, the radiation source 101 starts irradiation of radiation (step S109), and repeats irradiation of radiation at a frame rate according to the set imaging mode.

In step S110, after the first irradiation of radiation, the radiation imaging apparatus 102 acquires first image data X1 and holds it in an image data acquisition unit 201. Then, in step S111, the radiation imaging apparatus 102 acquires first correction image data D1 and stores it in a correction image data acquisition unit 202 before the second irradiation of radiation.

Subsequently, after the second irradiation of radiation, the radiation imaging apparatus 102 acquires second image data X2, and acquires second correction image data D2 before the third irradiation of radiation. In this manner, acquisition of image data generated during irradiation of radiation and acquisition of correction image data are performed in a period of one frame.

In step S112, the processing unit 204 performs offset correction processing using the first image data and the first correction image data. For example, offset correction processing is performed by subtracting the first correction image data from the first image data. Similarly, offset correction processing is performed using the second image data and the second correction image data.

Next, the operation performed when the imaging mode B' is set will be described. After the acquisition mode for acquiring correction data used for performing offset correction is determined to be the "11" mode by the determination unit 203 in step S108, the radiation imaging apparatus 102 acquires non-irradiation image data D1 to D4 before irradiation of radiation. The acquired correction image data D1 to D4 may be held in the correction image data acquisition unit 202, or may be held in another storage unit arranged in the radiation imaging apparatus 102. The non-irradiation image data may be acquired before the acquisition mode is determined, for example, during a reset operation of repeatedly resetting the pixel PIX arranged in the pixel array 220 before irradiation of radiation.

The radiation imaging apparatus 102 generates correction image data D using the non-irradiation image data D1 to D4, for example, by adding and averaging them, and holds the correction image data D in the correction image data acquisition unit 202. In this manner, correction image data is generated from a plurality of image data.

Then, when the user presses the exposure switch, the radiation source 101 starts irradiation of radiation (step S109) and repeats irradiation of radiation at a frame rate according to the set imaging mode.

In step S110, after the first irradiation of radiation, the radiation imaging apparatus 102 acquires the first image data X1 and stores it in the image data acquisition unit 201. Further, after the second irradiation of radiation, the radiation imaging apparatus 102 acquires the second radiation image data X2 and holds it in the image data acquisition unit 201. Acquisition of image data is repeated at a predetermined frame rate while the exposure switch is pressed.

In step S112, the processing unit 204 performs offset correction processing on the first image data X1 and the second image data X2 using the correction image data D. That is, in the imaging mode B', each image data is corrected using the same correction image data D and is output from the radiation imaging apparatus 102 as radiation image data.

As has been described above, in this embodiment, it is possible to perform the optimum offset correction processing in accordance with the imaging mode including the imaging condition, the irradiation condition, and the object information. Therefore, not only under a condition in which it is difficult to secure the S/N ratio but also under a condition in which the influence of an afterimage of the obtained radiation image is large, the accuracy of offset correction can be increased and the image quality of the obtained radiation image can be improved.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-130436, filed Jul. 12, 2019, which is hereby incorporated by reference herein in its entirety.

What is claimed is:

1. A radiation imaging apparatus, comprising:
a plurality of pixels configured to acquire a radiation image; and
a readout circuit configured to read out a plurality of signals from the plurality of pixels, wherein
correction image data used for performing offset correction is acquired from the plurality of pixels in an acquisition mode, which is defined by an estimated value based on at least one of the plurality of signals output from the plurality of pixels based on an imaging mode set by a user, and system noise to be generated when the readout circuit reads out the plurality of signals.

2. The apparatus according to claim 1, wherein the acquisition mode includes a first mode in which the correction image data is acquired based on a plurality of first image data obtained without irradiation of radiation, and a second mode in which the correction image data is acquired based on one second image data obtained without radiation of irradiation,
the correction image data is acquired in the first mode when the estimated value is not larger than a first predetermined threshold value, and
the correction image data is acquired in the second mode when the estimated value is larger than the first threshold value.

3. The apparatus according to claim 1, wherein the estimated value is associated with at least one of the number of binning upon capturing a radiation image, a gain upon amplifying a signal output from each of the plurality of pixels, a target dose in a region of interest, object information, a tube current of a radiation source that irradiates the radiation imaging apparatus with radiation, a tube voltage of the radiation source, or a radiation irradiation time, all of which are included in the imaging mode.

4. The apparatus according to claim 1, wherein the acquisition mode is associated with a frame rate upon capturing a radiation image based on the imaging mode.

5. The apparatus according to claim 1, wherein the acquisition mode is associated with contrast information of a radiation image estimated based on the imaging mode.

6. A radiation imaging apparatus, comprising:
a plurality of pixels configured to acquire a radiation image; and
a determination unit configured to determine an acquisition mode for acquiring correction image data from the plurality of pixels to perform offset correction, wherein
the acquisition mode includes a first mode in which the correction image data is acquired based on a plurality of image data obtained without irradiation of radiation, and a second mode in which the correction image data is acquired based on one second image data obtained without radiation of irradiation, and
the determination unit acquires an estimated incident dose based on an imaging mode set by a user, (i) determines the acquisition mode to be the first mode when the incident dose is not larger than a preset first threshold value, and (ii) determines the acquisition mode to be the second mode when the incident dose is larger than the preset first threshold value.

7. The apparatus according to claim 6, further comprising a readout circuit configured to read out a plurality of signals from the plurality of pixels, wherein
the first threshold value is set in accordance with system noise generated when the readout circuit reads out the plurality of signals from each of the plurality of pixels.

8. The apparatus according to claim 6, wherein the incident dose is acquired based on at least one of the number of binning upon capturing a radiation image, a gain upon amplifying a signal output from each of the plurality of pixels, a target dose in a region of interest, object information, a tube current of a radiation source that irradiates the radiation imaging apparatus with radiation, a tube voltage of the radiation source, or a radiation irradiation time, all of which are included in the imaging mode.

9. The apparatus according to claim 6, wherein the determination unit determines the acquisition mode further based on a frame rate upon capturing a radiation image.

10. The apparatus according to claim 9, wherein the determination unit (i) determines the acquisition mode to be the first mode if the frame rate is higher than a preset second threshold value, (ii) determines the acquisition mode to be the second mode when the frame rate is not higher than the preset second threshold value and the incident dose is larger than the first threshold value, and (iii) determines the acquisition mode to be the first mode when the frame rate is not higher than the second threshold value and the incident dose is not larger than the first threshold value.

11. The apparatus according to claim 6, wherein the determination unit determines the acquisition mode further based on contrast information of a radiation image estimated from the imaging mode set by the user.

12. The apparatus according to claim 10, wherein the determination unit determines the acquisition mode further based on contrast information of a radiation image estimated from the imaging mode set by the user, and
the determination unit (i) determines the acquisition mode to be the first mode when the frame rate is higher than the preset second threshold value, (ii) determines the acquisition mode to be the second mode when the frame rate is not higher than the second threshold value and a contrast corresponding value based on the contrast information is larger than a preset third threshold value, (iii) determines the acquisition mode to be the second mode when the frame rate is not higher than the second threshold value, the contrast corresponding value is not larger than the preset third threshold value, and the incident dose is larger than the first threshold value, and (iv) determines the acquisition mode to be the first mode when the frame rate is not higher than the second threshold value, the contrast corresponding value is not larger than the preset third threshold value, and the incident dose is not larger than the first threshold value.

13. The apparatus according to claim 5, wherein the contrast information includes at least one of an image size of a radiation image, a tube voltage of a radiation source that irradiates the radiation imaging apparatus with radiation, object information, or information of a gain upon amplifying a signal output from each of the plurality of pixels, all of which included in the imaging mode.

14. A radiation imaging system, comprising:
the radiation imaging apparatus according to claim 1; and
a radiation source configured to irradiate the radiation imaging apparatus with radiation.

15. A control method of a radiation imaging apparatus including a plurality of pixels configured to acquire a radiation image, and a readout circuit configured to read out a plurality of signals from the plurality of pixels, comprising:
acquiring, to perform offset correction, correction image data from the plurality of pixels in an acquisition mode, which is defined by an estimated value based on at least one of the plurality of signals output from the plurality of pixels based on an imaging mode set by a user, and system noise generated when the readout circuit reads out the plurality of signals.

16. A non-transitory computer-readable storage medium storing a program for causing a computer to execute a control method of a radiation imaging apparatus including a plurality of pixels used to acquire a radiation image, and a readout circuit configured to read out a plurality of signals from the plurality of pixels, comprising:
acquiring, to perform offset correction, correction image data from the plurality of pixels in an acquisition mode, which is defined by an estimated value based on at least one of the plurality of signals output from the plurality of pixels based on an imaging mode set by a user, and system noise generated when the readout circuit reads out the plurality of signals.

* * * * *